Figure 1:
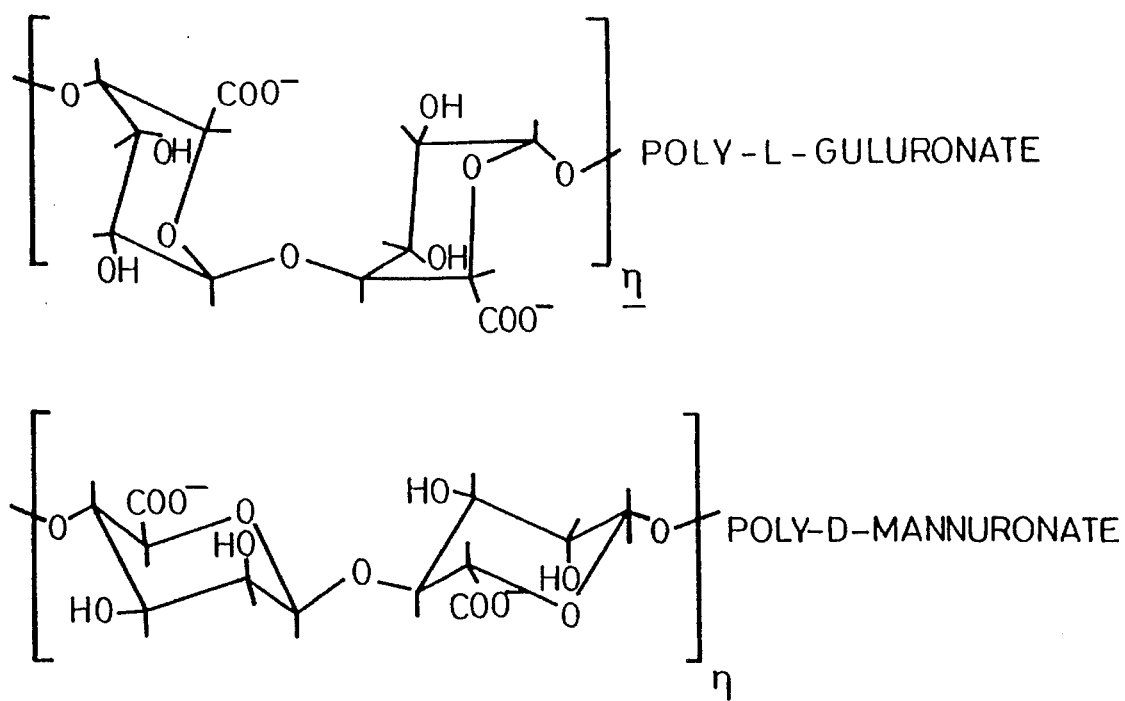

United States Patent [19]

Solomon et al.

[11] Patent Number: 5,484,604
[45] Date of Patent: Jan. 16, 1996

[54] CROSS-LINKED ALGINATE TRANSDERMAL MEDICINE DELIVERY DEVICES

[75] Inventors: Montague C. Solomon; Biljana Oraceska, both of London, England

[73] Assignee: Chatfield Pharmaceuticals Limited, Kramer Mews, England

[21] Appl. No.: 366,406

[22] Filed: Dec. 29, 1994

Related U.S. Application Data

[63] Continuation of Ser. No. 88,406, Jul. 7, 1993, abandoned, which is a continuation of Ser. No. 732,670, Sep. 19, 1991, abandoned.

[30] Foreign Application Priority Data

Jul. 21, 1991 [GB] United Kingdom ............... 9016056

[51] Int. Cl.$^6$ ........................... A61K 9/70; A61K 31/465
[52] U.S. Cl. ..................... 424/449; 424/484; 424/445; 514/343; 514/813
[58] Field of Search ................... 424/445, 449, 424/484; 514/343, 813

[56] References Cited

U.S. PATENT DOCUMENTS

| | | | |
|---|---|---|---|
| 3,938,515 | 2/1976 | Leeper | 424/449 |
| 3,962,414 | 6/1976 | Michaels | 424/427 |
| 3,996,934 | 12/1976 | Zaffaroni | 424/447 |
| 4,837,024 | 6/1989 | Michaeli | 424/446 |
| 4,983,395 | 1/1991 | Chang | 424/449 |
| 5,028,435 | 7/1991 | Katz | 424/449 |
| 5,064,422 | 11/1991 | Wick | 424/449 |

FOREIGN PATENT DOCUMENTS

| | | | |
|---|---|---|---|
| 1135625 | 11/1982 | Canada | 424/449 |
| 0099758 | 2/1984 | European Pat. Off. . | |
| 139127 | 5/1985 | European Pat. Off. | 424/449 |
| 186071 | 7/1986 | European Pat. Off. | 424/449 |
| 0289342 | 11/1988 | European Pat. Off. . | |
| 0307187 | 3/1989 | European Pat. Off. . | |
| 3319469 | 11/1984 | Germany | 424/449 |
| 54-151115 | 11/1979 | Japan . | |
| 1375572 | 11/1974 | United Kingdom | 424/445 |
| 02300 | 10/1980 | WIPO . | |
| 03705 | 9/1984 | WIPO . | |

OTHER PUBLICATIONS

Budavari, S. (1989), The Merck Index. (Eleventh edition). Merck & Co., Inc. pp. 41–42.

Genarro, A. R. (1985), Remington's Pharmaceutical Sciences. Mack Publishing Co., pp. 1296–1297.

Hensyl, W. R. (1990). Stedman's Medical Dictionary (25th edition). Williams and Wilkins Publishers, pp. 33 and 43.

*Primary Examiner*—Raj Bawa
*Attorney, Agent, or Firm*—Kalish & Gilster

[57] ABSTRACT

A process for preparing a transdermal drug delivery device includes preparing a polymer matrix by homogenizing about 7 weight % sodium alginate with about 3.5 weight % glycerol for about 5 minutes, mixing with about 0.5 weight % nicotine in about 89 weight % distilled water, casting the mixture over a backing material and drying overnight, and spraying with an about 5 weight % solution of calcium ions to cross-link. A control release membrane is prepared by homogenizing about 3.1 weight % of sodium alginate with about 3.6 weight % of glycerol for about 5 minutes, mixing with about 93.3 weight % of distilled water, casting the mixture over a backing material and drying overnight, and spraying with an about 5 weight % solution of calcium ions to cross-link. And, the drug delivery device is assembled by cutting a circle of the polymer matrix and a circle of the control release membrane and assembling them in sequence on a piece of backing material.

3 Claims, 2 Drawing Sheets

5,484,604

CROSS-LINKED ALGINATE TRANSDERMAL MEDICINE DELIVERY DEVICES

This application is a continuation of application Ser. No. 08/088,406, filed Jul. 7, 1993, now abandoned, which is a continuation of application Ser. No. 07/732,670, filed Jul. 19, 1991, now abandoned.

TECHNICAL FIELD

The invention relates to devices whereby medicaments can be administered through intact skin to the human or animal body. The medicine is absorbed into the blood circulation and transported to target tissue. By avoiding first pass, bioavailability is increased, therapeutic efficacy can be optimized, and side effects reduced.

BACKGROUND ART

A medicated plaster may comprise a backing material coated with an adhesive, and a reservoir of medicine adhering to a central part of the backing. The backing material should be impermeable to the medicine. When the periphery of the backing adheres to the skin, the reservoir of medicine is contacted with the skin, and the medicine permeates the skin.

The reservoir may comprise a hydrophilic or lipophilic polymer matrix in which the medicine is dispersed. The medicated polymer can be molded into a disc of determined surface area and thickness. The release of the medicine is governed by its diffusivity in the matrix and absorbability by the skin. The problem is to design a therapeutic system in which the skin penetration rate is determined by the rate at which the medicine is delivered to the skin surface and not the inherent permeability of the skin. See Patent Specifications U.S. 4,031,894 and EP 33615A2.

THE INVENTION

A device according to the invention comprises an alginic acid polymer matrix having a medicine dispersed therein, and an alginic acid polymer membrane for controlling the rate of release of the medicine from the matrix. The device may include means for keeping the membrane in contact with the skin, such as an adhesive plaster or bandage.

The alginic acid polymer is biodegradable, and should be selected having regard to its chemical and physical reactivity with the medicine. Molecular and structural factors such as polarity, hydrogen bonding, glass transition temperature, and the diffusivity of the medicine in the polymer are important. The alginic acid molecule is a long chain of uronic acid units joined by 1,4-glycosidic linkages. Thus it is a polyuronic acid made up of D-mannuronic and L-guluronic acid residues. The proportion of mannuronic and guluronic acid residues (the M/G ratio) determines the release behavior of the polymer with respect to the medicine: a faster release after swelling was found with a higher M/G ratio. Alginic acid salts with alkali metals, ammonia, magnesium and many organic bases are soluble in water, while those with most di- and polyvalent metals are insoluble. Calcium is most widely used for changing the viscosity and gel characteristics of algin solutions.

The medicine dispersed in the polymer matrix may for example be nicotine, which has high skin permeability and is used medically in this way to reduce the effects of nicotine withdrawal on cessation of smoking, diltiazem, verapamil, nifedipine or prazosin. The medicine can be incorporated in the polymer matrix by mixing a solution of the medicine with the polymer. The polymer may be partly cross-linked, for example, by the introduction of calcium, copper, chromium or like divalent metal, ions to form the three-dimensional polymer matrix. The resulting matrix can be cast or spread on the backing material and allowed to dry. The cross-linking can be completed by spraying a di- or polyvalent salt solution on the dry polymer matrix. A 5% aqueous solution of calcium, copper or chromium ions is suitable for this purpose. The membrane for controlling the rate of release of the medicine from the polymer matrix may be a polymer similar to that in the matrix. The polymer control release membrane can be cross-linked as described above to form an insoluble film.

The polymers are natural, inexpensive, non-toxic and biodegradable. They may be used as the carrier matrix, or as the control release membrane, or both in a transdermal delivery system. The release rate from the transdermal delivery system can be controlled by the polymer concentration, drug concentration, control release membrane thickness, and cross-linking with metal ions.

DRAWINGS

Figure 2:
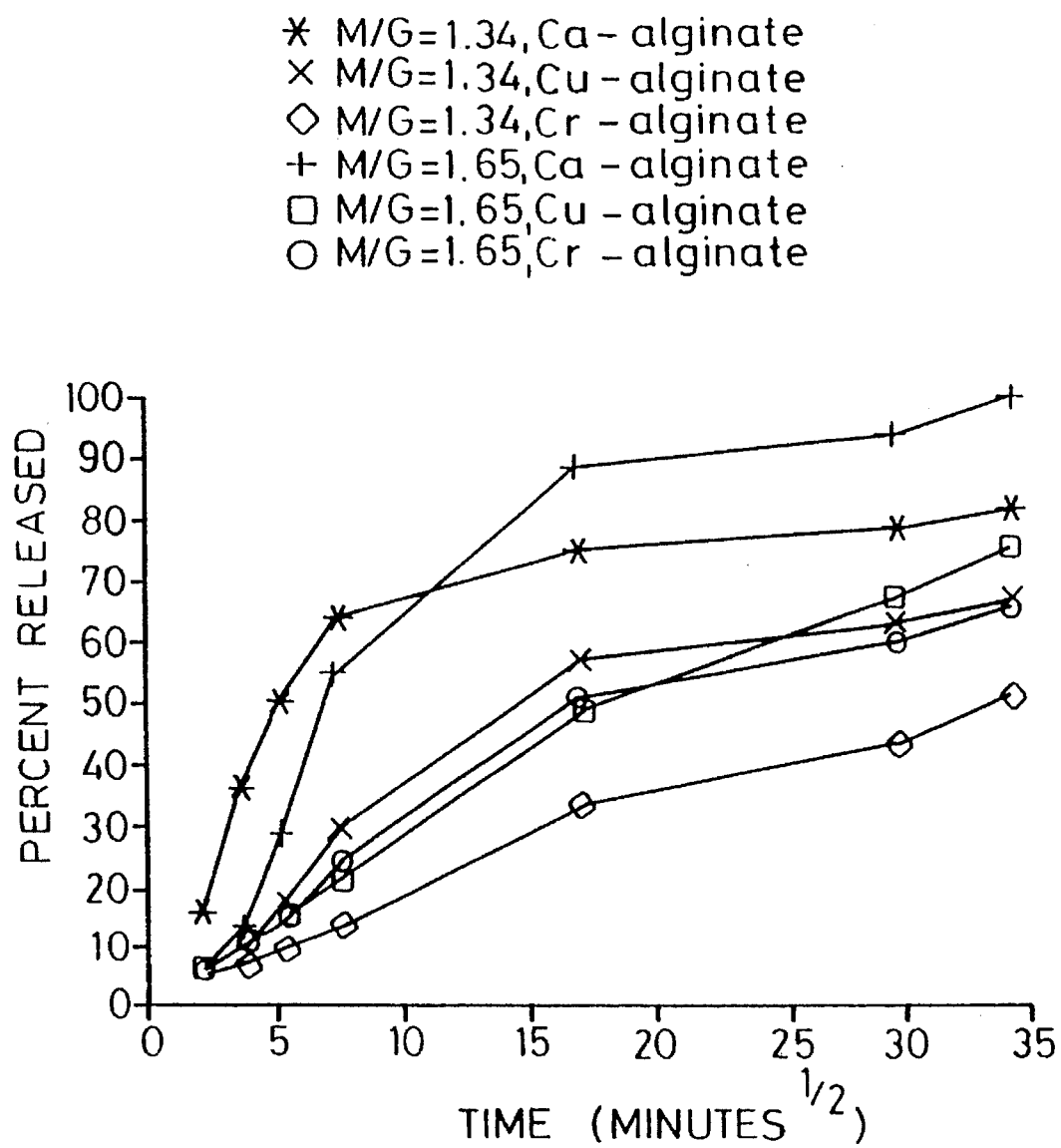

FIG. 1 shows the structural formulae of poly-L-gulronate and poly-D-mannuric blocks comprising mixed sequences of which make up alginate polymers; and FIG. 2 is a graph showing the percentages of nicotine released against time from a number of different alginate polymers matrices at 37° C. as determined in a Franz-type diffusion cell.

EXAMPLE

Polymer Matrix 7 g sodium alginate was homogenized with 3.5 g glycerol for 5 minutes. 0.5 g nicotine base was dissolved in 89 g distilled water. The homogenized alginate was mixed with the nicotine solution. The resulting viscous solution was cast using a thin layer chromatography spreader over a backing material and left overnight to dry. A 5% aqueous solution of calcium ions was sprayed over the dry alginate film, and left overnight to allow cross-linking to be completed. The resulting cross-linked film was cut into 3 cm diameter circles and stored in a desiccator.

Control Release Membrane 3 g sodium alginate was homogenized with 3.5 g glycerol for 5 minutes and mixed with 89.5 g distilled water in the absence of any medicine. The resultant viscous solution was cast using a thin layer chromatography spreader over a backing material and left overnight to dry. A 5% aqueous solution of calcium ions was sprayed on the dry film. The film was left overnight to allow cross-linking to be completed. The cross-linked film was cut into 3 cm diameter circles and stored in a desiccator.

A device for transdermal delivery of the nicotine through intact skin was assembled by placing a circle of the polymer matrix and a circle of the control release membrane in sequence on a piece of backing material so that the matrix was held in position by the control release membrane. The device could then be applied to the skin of a patient by contact through the membrane, which was held in place by an adhesive contacting the surrounding skin.

Release of the medicine comprises an initial burst as a result of hydration of the polymer matrix particularly when the amount of medicine in the polymer matrix was large. This was followed by steady state permeation with square root release kinetics. The initial burst is believed to be due to medicine present on the surface of the matrix resulting from the drying of the solution in the preparation process. In the steady state permeation, the medicine diffuses through pores in the matrix which is much slower. When the control release membrane is added to the device, the initial burst is suppressed due to the control release properties of the membrane, and this release follows with square root of time release kinetics.

We claim:

1. A process for preparing a transdermal drug delivery device comprising:

(A) preparing a polymer matrix by homogenizing about 7 weight % sodium alginate with about 3.5 weight % glycerol for about 5 minutes, mixing with about 0.5 weight % nicotine in about 89 weight % distilled water, casting the mixture over a backing material and drying overnight, and spraying with an about 5 weight % solution of calcium ions to cross-link; and (B) preparing a control release membrane by homogenizing about 3.1 weight % of sodium alginate with about 3.6 weight % of glycerol for about 5 minutes, mixing with about 93.3 weight % of distilled water, casting the mixture over a backing material and drying overnight, and spraying with an about 5 weight % solution of calcium ions to cross-link; and (C) assembling the device by cutting a circle of the polymer matrix and a circle of the control release membrane and assembling them in sequence on a piece of backing material.

2. The process of claim 1, wherein the transdermal drug delivery device is applied to the skin of a patient by contact through the membrane, wherein the device is held in place by an adhesive contacting the surrounding skin.

3. A transdermal drug delivery device for use as an aid to giving up smoking consisting of:

(A) a polymer matrix consisting of a mixture of about 7 weight % sodium alginate, about 3.5 weight % glycerol, about 0.5 weight % nicotine, about 89 weight % distilled water, cross-linked with an about 5 weight % solution of calcium ions and dried overnight; and (B) a control release membrane consisting of a mixture of about 3.1 weight % of sodium alginate, about 3.6 weight % of glycerol and about 93.3 weight % of distilled water, cross-linked with an about 5 weight % solution of calcium ions and dried overnight; wherein, (C) a cut circle of the polymer matrix is placed on a backing material and a cut circle of the control release membrane is placed on the polymer matrix.

\* \* \* \* \*